US00PP12710P2

(12) United States Plant Patent
Holder

(10) Patent No.: US PP12,710 P2
(45) Date of Patent: Jun. 18, 2002

(54) SUGAR CANE VARIETY 'CL83-4266'

(75) Inventor: David G. Holder, Clewiston, FL (US)

(73) Assignee: U.S. Sugar Corporation, Clewiston, FL (US)

( * ) Notice: Subject to any disclaimer, the term of this patent is extended or adjusted under 35 U.S.C. 154(b) by 0 days.

(21) Appl. No.: 09/387,972

(22) Filed: Sep. 1, 1999

(51) Int. Cl.[7] ..... A01H 5/00
(52) U.S. Cl. ..... Plt./385
(58) Field of Search ..... Plt./385

(56) References Cited

PUBLICATIONS

Holder, D.G., and E.H. Todd [1981] "Registration of CL 61–620 Sugarcane (Reg. No. 53)", *Crop Sci. Soc. Of Am.* 21:634.

*Primary Examiner*—Bruce R. Campell
*Assistant Examiner*—Annette H. Para
(74) *Attorney, Agent, or Firm*—Saliwanchik, Lloyd & Saliwanchik

(57) ABSTRACT

A new and distinct variety of sugar cane has resulted from crossing the variety of 'CL66-141' (unpatented) as a female with variety 'CL73-838' (unpatented) as male.

6 Drawing Sheets

BACKGROUND OF THE INVENTION

This new variety of *Saccharum officinarum*, commonly known as sugar cane, with the identifying number CL83-4266 originated as a seedling from a true seed produced by the inventor by crossing the variety CL66-141 (unpatented) as a female with variety CL73-838 (unpatented) as male. In this form of variety designation, which is well known to sugar cane breeders, 'CL' denotes the breeding locality or station, i.e. Clewiston, Fla.; 83 represents the year that the particular variety was first grown in the field, i.e. 1983; and 4266 is the distinctive number assigned to that variety among those grown in that year. The cross was made in December 1982, at Clewiston, Fla., and this new variety was selected from among the progeny of the cross. The inventor has subsequently asexually reproduced the new variety at Clewiston, Fla., by means of stem cuttings. The new variety does not produce seeds under typical field conditions.

The new variety has acceptable sucrose levels beginning in December and maintains a high level of sucrose throughout the rest of the harvest season (a typical harvest season is November 1 to March 15), produces high tons per acre of cane and high tons per acre of sugar. In replicated trials (Table 1) the new clone was compared to a standard cultivar CL61-620 (unpatented; Holder, D. G., and E. H. Todd, 1981, Registration of CL61-620 Sugarcane: Registration Number 53, Crop Science, volume 21, Number 4, page 634; and Glaz, Barry, 1998, Sugarcane Variety Census: Florida 1998, Sugar Azucar, volume 93, Number 12, pages 30–37). In the replicated trial on a medium mineral Terra Ceia organic soil, the new clone averaged lower in early percent yield of sucrose (yield of 96° sucrose, percent cane), higher in late percent yield of sucrose, lower in tons per acre of cane, and lower in both early and late tons per acre of sucrose than 'CL61-620'. In the trial on a low mineral Terra Ceia organic soil, the new clone averaged lower for early percent yield of sucrose, higher in late percent yield of sucrose, lower in tons per acre of cane, lower in early tons per acre of sucrose, and higher in late tons per acre of sucrose than 'CL61-620'.

The new clone was competitive with standard cultivars in outfield tests on farms. These tests were designed for a practical demonstration of the potential of the new clone rather than for statistical comparison. The outfield plots, which were several acres in size, were distributed over variable environmental years, organic soil types, planting dates, and harvest dates. The mean production of the new clone was compared with that of standard cultivars grown in surrounding fields on the farms (Table 2). 'CL83-4266' exceeded cultivar CL69-886 (unpatented; and Glaz, Barry, 1998, Sugarcane Variety Census: Florida 1998, Sugar Azucar, volume 93, Number 12, pages 30–37) for sucrose content, tons per acre of cane, and tons per acre of sucrose. 'CL83-4266', although a little lower in sucrose content, exceeded 'CL77-797' (U.S. Plant Pat. No. 10,839, Title: Sugar Cane Variety CL77-797, Issue Date: Mar. 23, 1999) for tons per acre of cane and tons per acre of sucrose.

The new variety is not recommended for growing on sandy soils.

On organic soils the mature stalks of CL83-4266 are longer but about equal in diameter to those of CL61-620. In the replicated trial on the medium mineral Terra Ceia soil the average stalk length was 23.7 decimeters vs 22.8 decimeters for CL61-620, and the average stalk diameter was 2.80 cm vs 2.75 cm, respectively. In the replicated trial on the low mineral Terra Ceia soil the average stalk length was 22.9 decimeters vs 21.3 decimeters for CL61-620, and the average stalk diameter was 2.70 cm vs 2.70, respectively. The stalk core is usually solid, but occasionally may have a small hole or pith.

In Florida the stalks of this new variety usually flower in high frequency in early December. The variety may flower in late November.

The new variety has a high fiber content of 13.0%.

Based on experimental tests and extensive field observations the new variety is judged to be resistant to several disease common to Florida. In inoculation tests the variety was highly resistant to smut (caused by *Ustilago scitaminea* Syd. and P. Syd.), tolerant to ratoon stunting disease (caused by *Clavibacter xyli* subsp. *xyli,* Davis), resistant to leaf scald (caused by *Xanthomonas albilineans* Ashby, Dowson), and resistant to sugarcane mosaic virus strains A, B, D, and E. In order to verify the inoculation tests, extensive observations were made and the variety was found to maintain its resistance to the four diseases above in field plots. Further, based on extensive field observations the new variety is judged to be resistant to rust disease (caused by *Puccinia melanocephala* Syd. and P. Syd.), eye spot disease (caused by *Bipolaris sacchari* (Butl.) Shoemaker), and brown stripe (caused by *Cochliobolus stenospilus* (Drechs.) Mat. and Yam. The new clone is resistant to natural infections of pokkah boeng (caused by *Fusarium moniliforme* Sheldon).

The stalks of the new clone begin to lodge as the crop matures and all are recumbent at time of harvest. The new variety is more recumbent than CL61-620 at harvest. Harvestability is rated as average. The new variety is harvested satisfactorily by the chopper type mechanical harvester currently in use in Florida. This one-row harvester is equipped with break-away crop divider points and scrolls (twin spiral crop dividers) which operate between the rows and direct cane to the throat of the harvester where the base cutters are located. The variety has not exhibited signs of brittleness.

TABLE 1

Productivity of CL83-4266 compared to commercial standard cultivar CL61-620, on two organic soil types. The data are expressed as the percentage the new clone was higher or lower than the standard clone for the production factors.

| Clonal | Yield of 96° sucrose percent cane | | Tons per acre of | Tons per acre of sucrose | |
|---|---|---|---|---|---|
| Comparison | Early[1] | Late[2] | cane | Early | Late |
| | Medium mineral Terra Ceia organic soil[3] | | | | |
| CL83-4266 vs. CL61-620 | −5.1% | +0.3% | −3.0% | −7.9% | −3.3% |
| | Low mineral Terra Ceia organic soil[4] | | | | |
| CL83-4266 vs. CL61-620 | −1.5% | +6.2% | −3.6% | −4.9% | +2.5% |

[1]Early determinations during November.
[2]Late determinations during January to February.
[3]Six replications per clone for two crops (i.e. the same plots were harvested annually for two years).
[4]Four replications per clone for three crops (i.e. the same plots were harvested annually for three years).

TABLE 2

Production of new clone CL83-4266 in outfield plots compared to standard cultivars grown in surrounding fields. The data are expressed as the percentage the new clone was higher or lower than the standard cultivar. The outfield plots were several acres in size and located on various organic soils. Each comparison is the mean of three plant crops, one successive-plant crop, and one first-stubble crop.

| Clonal Comparison | Yield 96° sucrose, percent cane | Tons per acre of cane | Tons per acre of sucrose |
|---|---|---|---|
| CL83-4266 vs. CL77-797 | −2.3% | +11.6% | +8.2% |
| CL83-4266 vs. CL69-886 | +7.4% | +12.5% | +19.8% |

DETAILED DESCRIPTION OF THE NEW VARIETY

Figure 1:
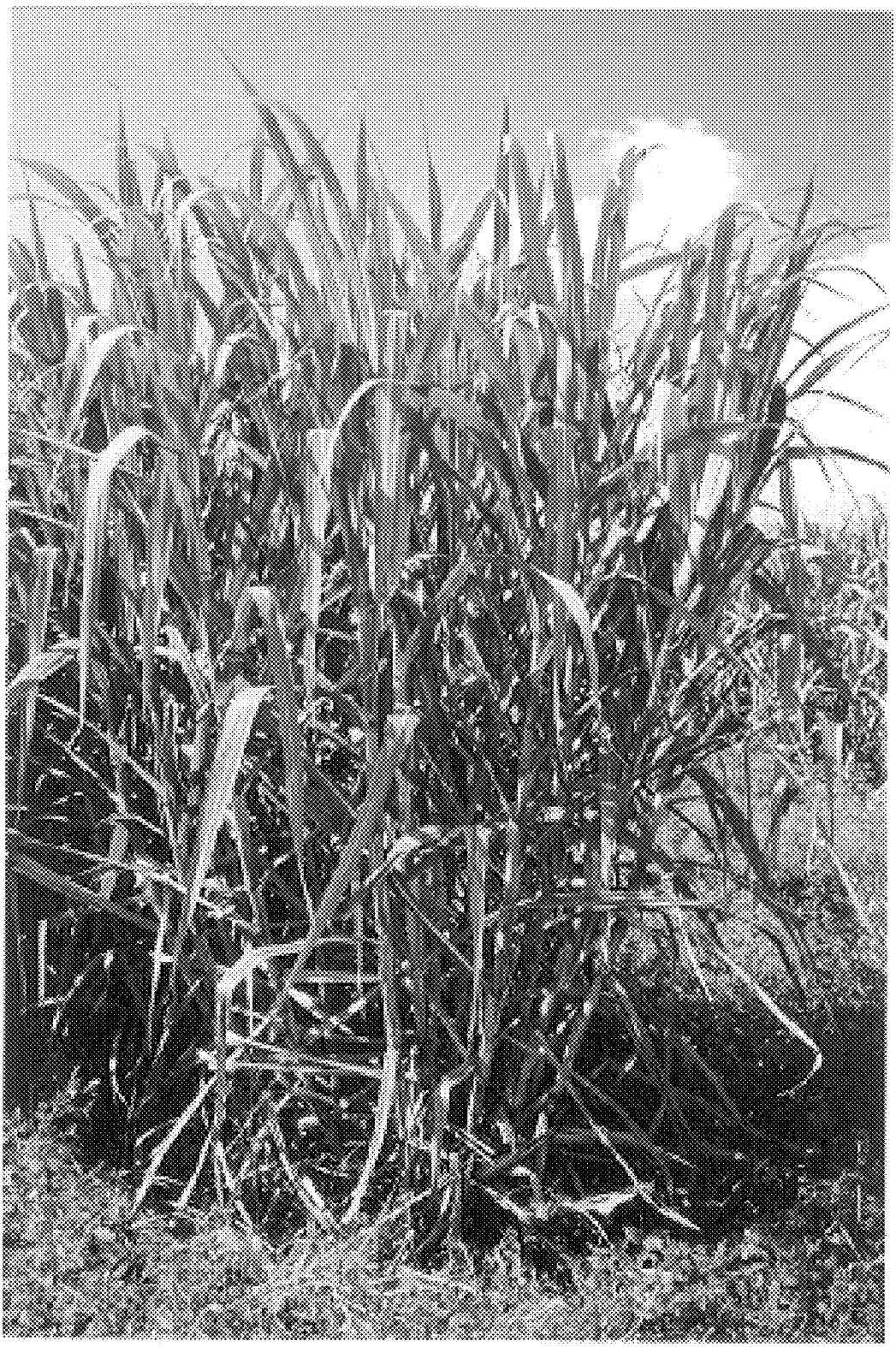
FIG. 1. Sugarcane variety CL83-4266. Picture taken Aug. 30, 1999 of sugarcane planted Oct. 9, 1998 near South Bay, Fla.
Figure 2:
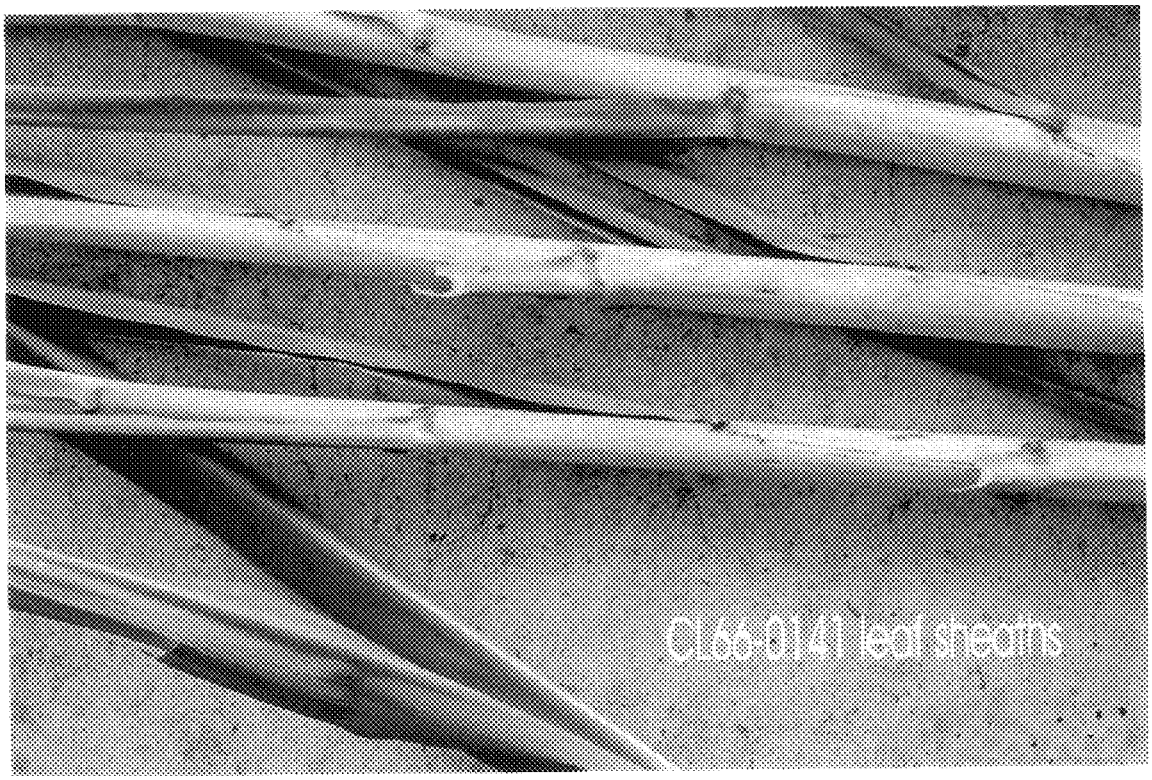
FIG. 2 depicts the leaf sheath, and its coloring, of parent variety 'CL66-0141'.
Figure 3:
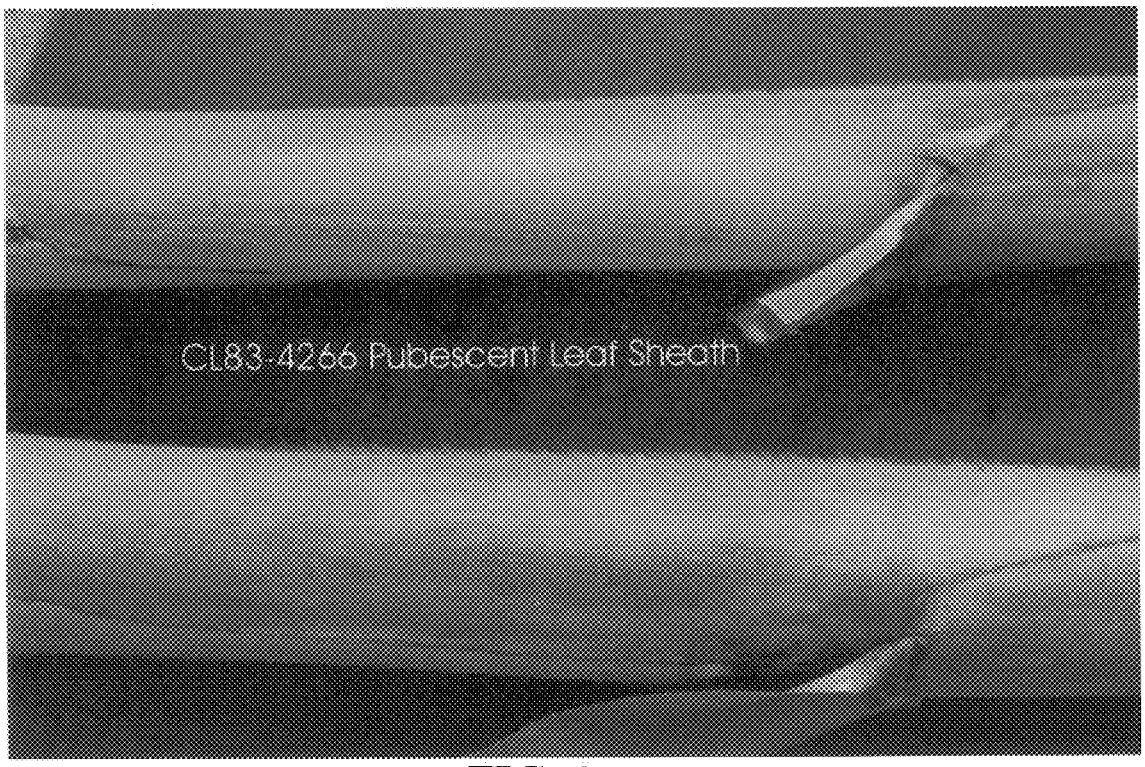
FIG. 3 depicts the leaf sheath, and its coloring, of the claimed sugar cane plant 'CL83-4266'.
Figure 4:
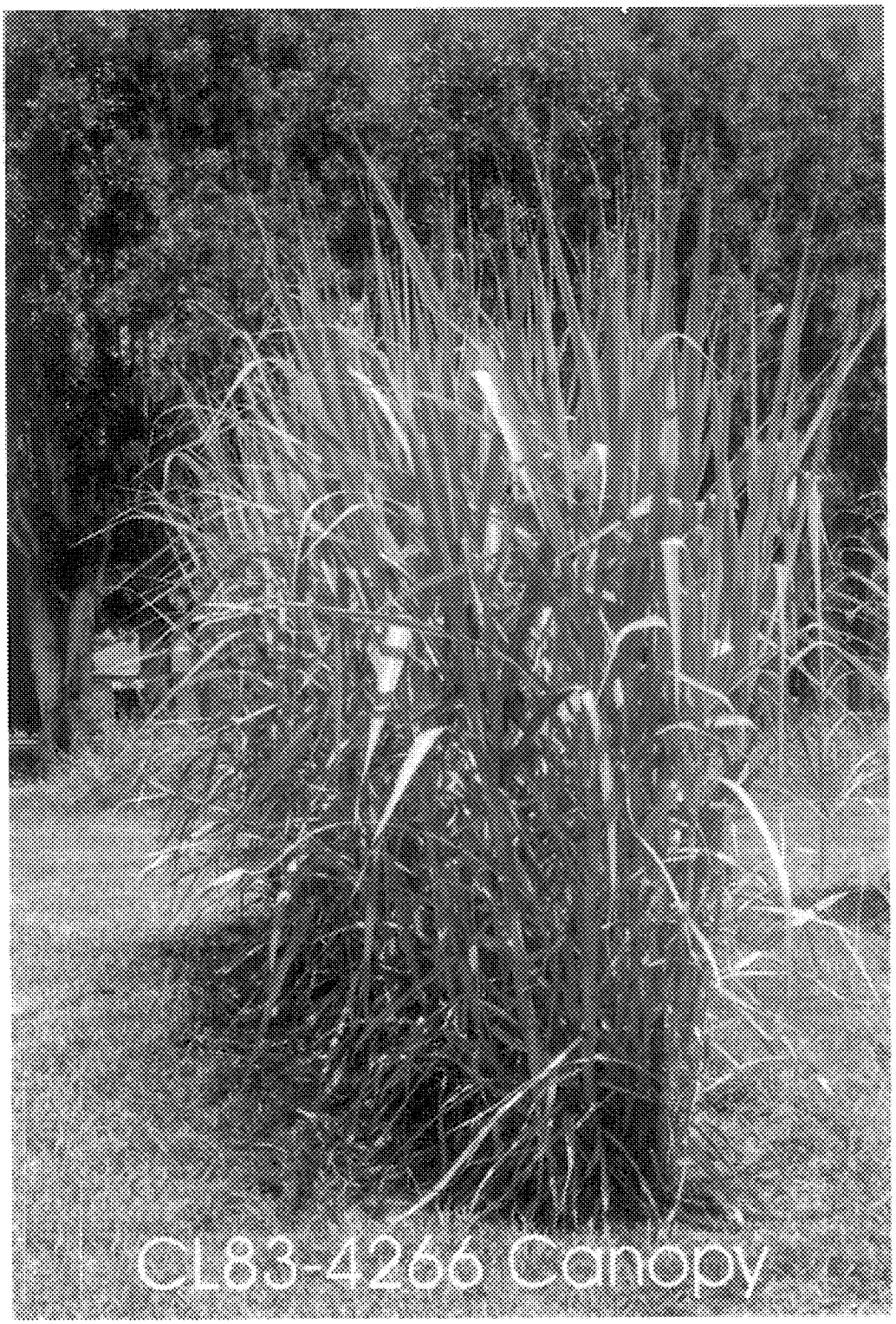
FIG. 4 depicts the canopy form of the claimed sugar cane plant 'CL83-4266'.
Figure 5:
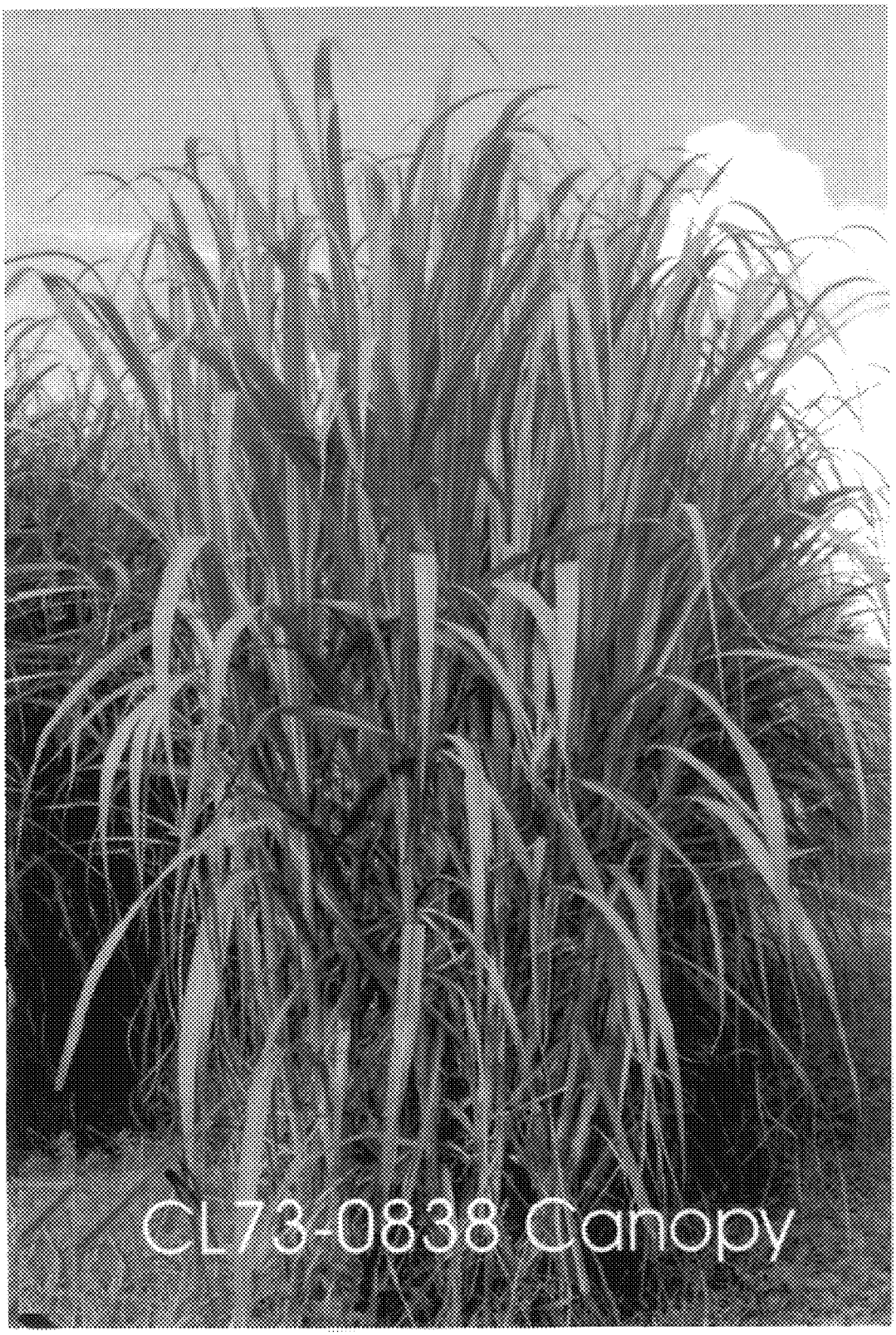
FIG. 5 depicts the canopy form of parent variety 'CL73-0838'.
Figure 6:
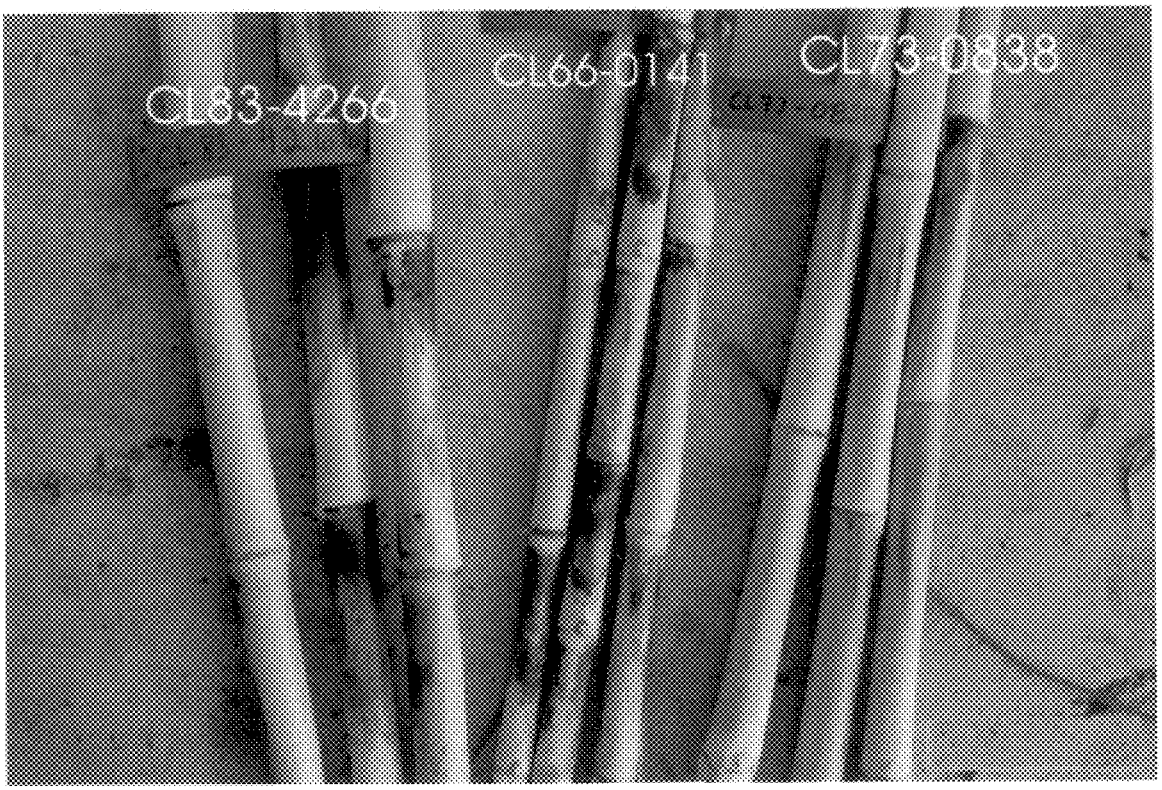
FIG. 6 depicts the coloring of the stalks of the parent varieties ('CL66-0141' and 'CL73-0838') and the claimed sugar cane plant 'CL83-4266'.

Parent variety 'CL66-0141' is most easily distinguished from variety CL83-4266 by its glaborous (lacking hair) leaf sheath (FIG. 2) as compared to the quite pubescent leaf sheath of 'CL83-4266' (FIG. 3). Other differences include a more even green colored leaf sheath for the parent ('CL66-0140', FIG. 2) as compared a green leaf sheath with red-purple mottling on the claimed cultivar (CL83-4266). 'CL73-0838' is distinguished from 'CL83-4266' by its more drooping leaf canopy (FIG. 4) as compared to the very erect and pointed leaf canopy for 'CL83-4266' (FIG. 5) The stalks of 'CL73-0838' are greener than the more yellow-hued stalks of 'CL83-4266' (FIG. 6).

Culm internodes mostly cylindrical, occasionally with a slightly concave outline, mostly medium green but becoming purple in age; mid-culm internodes 110 to 200 mm long (average 165 mm), 23 to 30 mm wide (average 28 mm); lower internodes 24 to 33 mm wide (average 30 mm); upper internodes 17 to 28 mm wide (average 25 mm). Wax bloom thin. Internode smooth, glabrous, mostly without corky cracks. Bud furrow not distinct. Growth ring glabrous, 2 to 4 mm wide, slightly depressed. Root band 9 to 12 mm wide, with 3 to 4 irregular rows of root primordia, with straight sides. Primordia irregular in shape, about 1 mm in diameter.

Buds inserted immediately above the leaf scar, generally pentagonal with a distinct wing on the upper half central, 8–11 mm long, 7–8.5 mm wide, becoming swollen and plump, light brown (distinctly darker in color than the surrounding root band). The central area glabrous, with a short membranous fringe formed by the margin overlap; the body or sides glabrous, and distinctly 21 to 29-nerved, the base with a few short hairs originating from the internerve areas; the body with nerves swollen and wider than the internode regions. The germ pore initially represented as a dark line about 1 mm long, at maturity becoming pronounced. The juncture about 0.5 mm wide, hairy, the hairs silver in color, 1 to 1.5 mm long. The wing 1 to 1.3 mm wide, glabrous or with a few short white hairs, the margins ciliate with relatively long setaceous hairs, the hairs unicellular 1.5 to 2 mm long.

Mid-culm leaf blades green in color, linear, 120 to 195 mm long (average 140 mm), 20 to 60 mm wide (average 33 mm), glabrous, with a smooth surface, relatively thin, chartaceous. Mid-rib pale in color, 4 to 8 mm wide, smooth and glabrous, distinctly raised on the abaxial surface, flat to concave on the adaxial surface. Blades with an acuminate apex and tapering to a truncate base. The margins with coarse antrosely curved strigose hairs. Leaf sheaths with a glabrous or sparsely pubescent body, the dorsal area usually with setaceous hairs about 2 mm long, glabrous at the base, and glabrous on the margins. Sheaths 160 425 mm long (average 210 mm), light green, pink to red, or straw-colored. Frequently straw-colored at the base, light red in the middle portions and becoming green towards the apex.

Collar region glabrous, differentiated by a green to dark green color and a heavier wax covering. Dewlap squarish in outline, generally hairy. Auricles straight to slopping transitional, green in color, the inner margin with long setaceous hairs. The area of the dewlap associated with the ligule is covered with a mixture of hair types. Pilose hairs about 0.2 mm long cover the entire area. Setaceous hairs about 1.0 mm long occur commonly in the region. Coarse setaceous hairs to 8 mm long are clustered at the margins. These coarse hairs become associated with the inner margin the auricle.

Ligule tan in color at maturity, initially membranous, becoming indurate at maturity, with a glabrous abaxial surface, crescent-shaped, 1.2 to 2.3 mm wide at the margins, 3.5 to 4.5 mm wide at the center, the apical margins irregular or torn, ciliate, the cilia 0.2 to 0.4 mm long. The adaxial surface of the ligule covered with silver, straight, appressed, setaceous hairs, the hairs about 1 mm long.

Inflorescence peduncle essentially pubescent throughout with short, appressed, silvery hairs, typically 7 to 8 mm wide, 65 to 85 mm long, degenerating from the base. Inflorescence main axis hairy, 60 to 80 mm long. Primary branches 100 to 250 mm long with appressed racemose branches. Rachis internodes glabrous or with a few setaceous hairs at the apex, 3.3 to 5 mm long, slightly grooved. Pedicels 1.5 to 3.0 mm long, glabrous except for a few apical hairs, apex cupuliform. Sessile spikelet with callus hairs 7 to 9 mm long, white in color, 3.1 to 4.0 mm long; lanceolate, acuminate; glumes membranous; lemma a hyaline scale; stamens 1 to 1.2 mm long, yellow to red in color. Pedicel spikelet ovate, acute, rounded at the base, 2.8 to 3.1 mm long; glumes membranous, lemma hyaline, stamens mostly yellow.

What is claimed is:

1. The new and distinct variety of sugar cane herein shown, described, and identified by the combination of the characteristics set forth above.

* * * * *

UNITED STATES PATENT AND TRADEMARK OFFICE

CERTIFICATE OF CORRECTION

PATENT NO. : PP 12,710 P2
DATED : June 18, 2002
INVENTOR(S) : David G. Holder

It is certified that error appears in the above-identified patent and that said Letters Patent is hereby corrected as shown below:

Column 2,
Line 35, “disease” should read -- diseases --.

Column 4,
Line 19, “5) The” should read -- 5). The --.

Signed and Sealed this

Thirty-first Day of December, 2002

JAMES E. ROGAN
*Director of the United States Patent and Trademark Office*